US00PP10996P

United States Patent [19]

Larsen et al.

[11] Patent Number: Plant 10,996

[45] Date of Patent: Jul. 6, 1999

[54] OSTEOSPERMUM PLANT NAMED 'SUNNY INGRID'

[75] Inventors: Bjarne Larsen; Niels Larsen, both of Odense N, Denmark

[73] Assignee: Paul Ecke Ranch, Encinitas, Calif.

[21] Appl. No.: 08/959,901

[22] Filed: Oct. 29, 1997

[51] Int. Cl.[6] ..... A01H 5/00

[52] U.S. Cl. ..... Plt./360

[58] Field of Search ..... Plt./68.1, 360

*Primary Examiner*—Howard J. Locker

*Assistant Examiner*—Melissa L. Kimball

*Attorney, Agent, or Firm*—C. A. Whealy

[57] ABSTRACT

A distinct cultivar of Osteospermum plant named 'Sunny Ingrid', characterized by its upright and outwardly spreading growth habit with dense foliage and erect flower stems; moderate growth rate; purple ray florets with violet blue disc florets; and numerous inflorescences per plant.

2 Drawing Sheets

The present invention relates to a new and distinct cultivar of Osteospermum plant, botanically known as *Osteospermum ecklonis* and referred to by the cultivar Sunny Ingrid. The new Osteospermum was tested under the name Sunny Ingrid.

The new cultivar is a product of a planned breeding program conducted by the inventors in Odense, Denmark. The objective of the breeding program was to create new Osteospermum cultivars having uniform plant habit and interesting floret colors and leaf shape.

The new cultivar originated from a cross made by the inventors of two *Osteospermum ecklonis* proprietary selections. The female, or seed, parent was identified as code number 2.72.93 and the male, or pollen, parent was identified as code number 2.61.93. The new Osteospermum was selected by the inventors from the progeny of this cross in a controlled environment in Odense, Denmark, in 1995. Plants of the new Osteospermum differ from plants of the parent selections in floret color.

Asexual reproduction of the new cultivar by terminal cuttings taken at Odense, Denmark, has shown that the unique features of this new Osteospermum are stable and reproduced true to type in successive generations.

The following traits have been repeatedly observed and are determined to be the unique characteristics of 'Sunny Ingrid'. These characteristics in combination distinguish 'Sunny Ingrid' as a new and distinct cultivar:

1. Upright and outwardly spreading growth habit with dense foliage and erect flower stems.
2. Moderate growth rate.
3. Purple ray florets with violet blue disc florets.
4. Numerous inflorescences per plant. Plants flower continuously.

The cultivar Sunny Ingrid has not been observed under all possible environmental conditions. The phenotype may vary somewhat with variations in environment such as temperature, daylength and light intensity, without, however, any variance in genotype.

Plants of the new Osteospermum can be compared to plants of the *Osteospermum ecklonis* cultivar Sunny Lady (disclosed in U.S. Plant Pat. No. 10,353). However, in side-by-side comparisons conducted in Odense, Denmark, and Keller, Tex., plants of the new Osteospermum were more compact, less spreading, and had stronger and more erect flower stems than plants of the cultivar Sunny Lady. Stems on plants of the cultivar Sunny Lady are purplish red whereas stems of plants of the cultivar Sunny Ingrid are green in color. In addition, peduncles on plants of the cultivar Sunny Lady are reddish towards the apex whereas peduncles of plants of the cultiar Sunny Ingrid are green in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical flowering plant of 'Sunny Ingrid'.

The photograph at the top of the second sheet is a close-up view of typical inflorescences (upper surface, left, and under surface, right) and leaves (center) of 'Sunny Ingrid'.

The photograph at the bottom of the second sheet comprises a comparison side perspective view of typical plants the cultivar Sunny Lady (left) and the cultivar Sunny Ingrid (right). Foliage and floret colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown outdoors in containers during the spring in Encinitas, Calif. and Keller, Tex. Measurements and numerical values represent averages for typical flowering plants.

Botanical classification: *Osteospermum ecklonis* cultivar Sunny Ingrid.

Parentage:

*Female, or seed, parent.*—Proprietary selection of *Osteospermum ecklonis*, code number 2.72.93.

*Male, or pollen, parent.*—Proprietary selection of *Osteospermum ecklonis*, code number 2.61.93.

Propagation:

*Type.*—Terminal tip cuttings.

*Time to initiate roots.*—Summer: About 14 days at 20° C. Winter: About 18 days at 20° C.

*Time to develop roots* (*time required to produce a rooted cutting*).—Summer: About 21 days at 20° C. Winter: About 28 days at 20° C.

*Rooting habit.*—Fine, fibrous and somewhat branched.

Plant description:

*Appearance.*—Perennial herbaceous container and garden plant. Rounded and outwardly spreading growth habit. Dense foliage and erect flower stems. Freely branching and growth rate is moderate.

*Plant height.*—About 40 cm.

*Plant spread.*—About 60 cm.

*Foliage description.*—Leaves alternate, single. Length, fully expanded leaves: About 7 cm. Width, fully expanded leaves: About 2.5 cm. Shape: Oblanceolate. Apex: Cuspidate. Base: Attenuate, leaves sessile. Margin: Widely-spaced teeth, 4 to 5 per edge. Aspect: Flat. Texture: Very fine pubescence on both surfaces and at margins. Fragrance: Strongly fragrant, typical of species. Color: Young foliage, upper surface: 146A. Young foliage, under surface: 146B. Fully expanded foliage, upper surface: 147A. Fully expanded foliage, under surface: 147B. Attenuated leaf base: Greenish white. Venation, upper surface: 146B. Venation, under surface: 146C.

Inflorescence description:

*Appearance.*—Daisy-type composite inflorescence form. Inflorescences borne on terminals above foliage, arising from leaf axils. Disc and ray florets arranged acropetally on a capitulum. One inflorescence per flowering stem. Inflorescences persistent.

*Flowering response.*—Under natural conditions, plants flower continuously from April to October in the Northern Hemisphere.

*Fragrance.*—Slight, typical of species.

*Inflorescence size.*—Diameter: About 6 cm. Depth (height): About 2 cm. Diameter of disc: About 1 cm.

*Opening inflorescences.*—Length: About 1.5 cm. Width: About 1 cm. Shape: Pointed. Color: Darker green than 144A.

*Ray florets.*—Length: About 3 cm. Width: About 7.5 mm. Shape: Oblanceolate. Apex: Rounded or sometimes emarginate with 3 lobes. Margin: Entire. Texture: Satiny, smooth. Number of ray florets per inflorescence: About 20. Color: When opening: 83B. Mature, upper surface: 80A, color will fade slightly to 80B with subsequent development. Mature, under surface: 80A/80B with darker stripes of 83A.

*Disc florets.*—Length: About 7 mm. Width: About 1 mm at base, flaring to about 2.5 at apex. Shape: Tubular, slightly funnel-shaped. Number of disc florets per inflorescence: Numerous. Color: Immature: 94A. Mature: 89A.

*Peduncle.*—Length: About 14 cm. Diameter: About 2 mm. Aspect: Strong, inflorescences held erect above foliage. Texture: Rough, slightly pubescent. Color: 144A.

*Sepals.*—Appressed to ray florets. Shape: Narrowly lanceolate with pointed apex. Quantity: About 20 per inflorescence. Texture: Rough with short coarse hairs. Color: 144A.

*Reproductive organs.*—Androecium: Present on disc florets only. Anthers: One per disc floret, 5-parted. Pollen: Golden yellow, moderate. Gynoecium: Present on ray and disc florets. Stigma: Bipartite. Style: Purple. Ovary: Inferior, green in color.

Disease resistance: No known Osteospermum diseases observed to date on plants grown under commercial production.

Seed production: Seed production has not been observed.

It is claimed:

1. A new and distinct cultivar of Osteospermum plant named 'Sunny Ingrid', as illustrated and described.

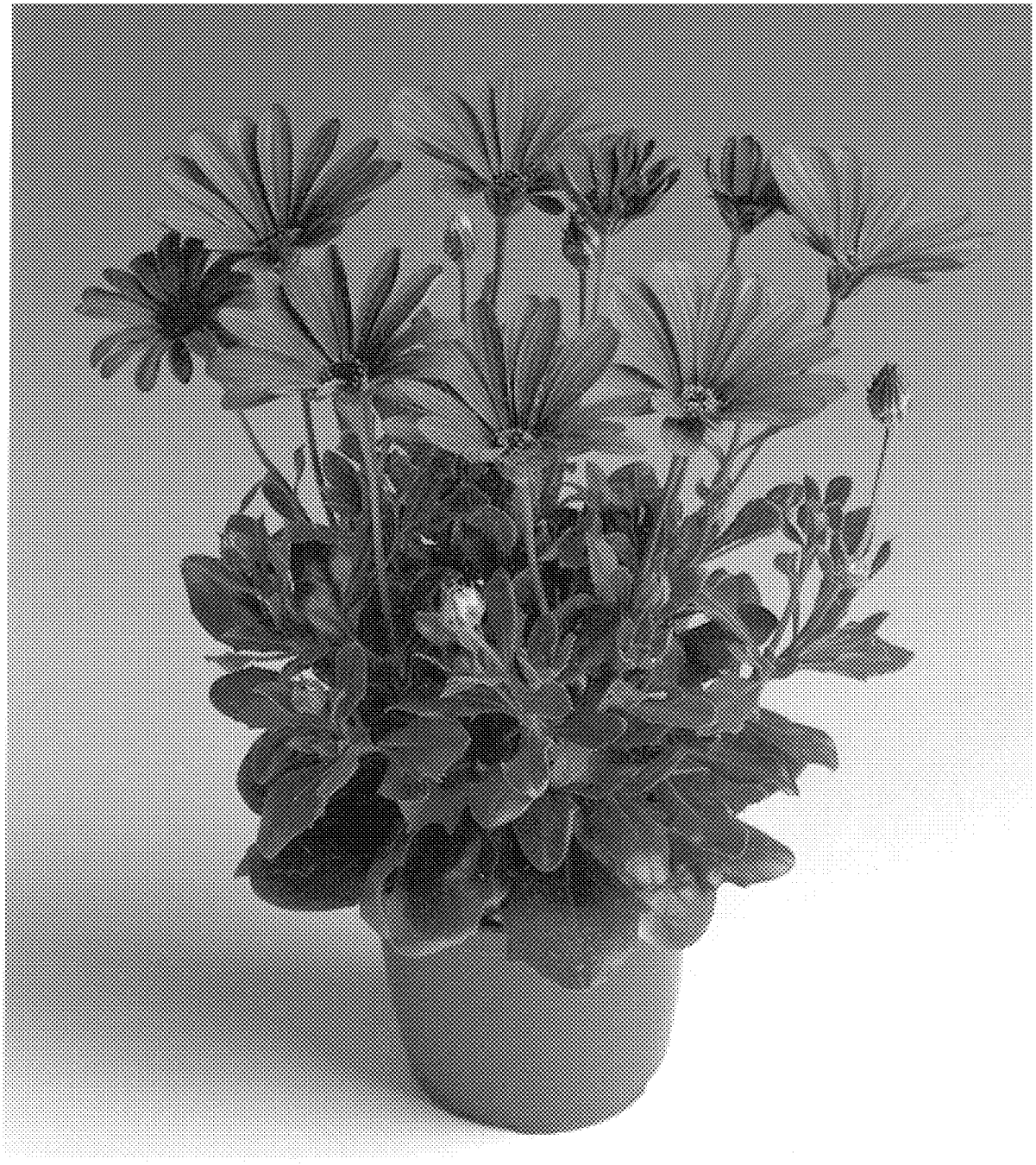

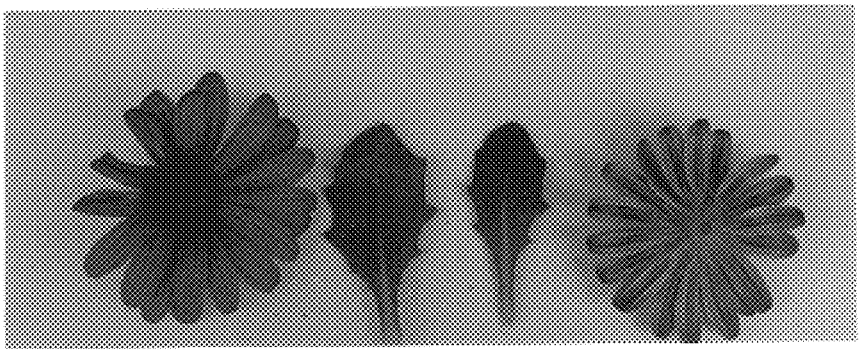
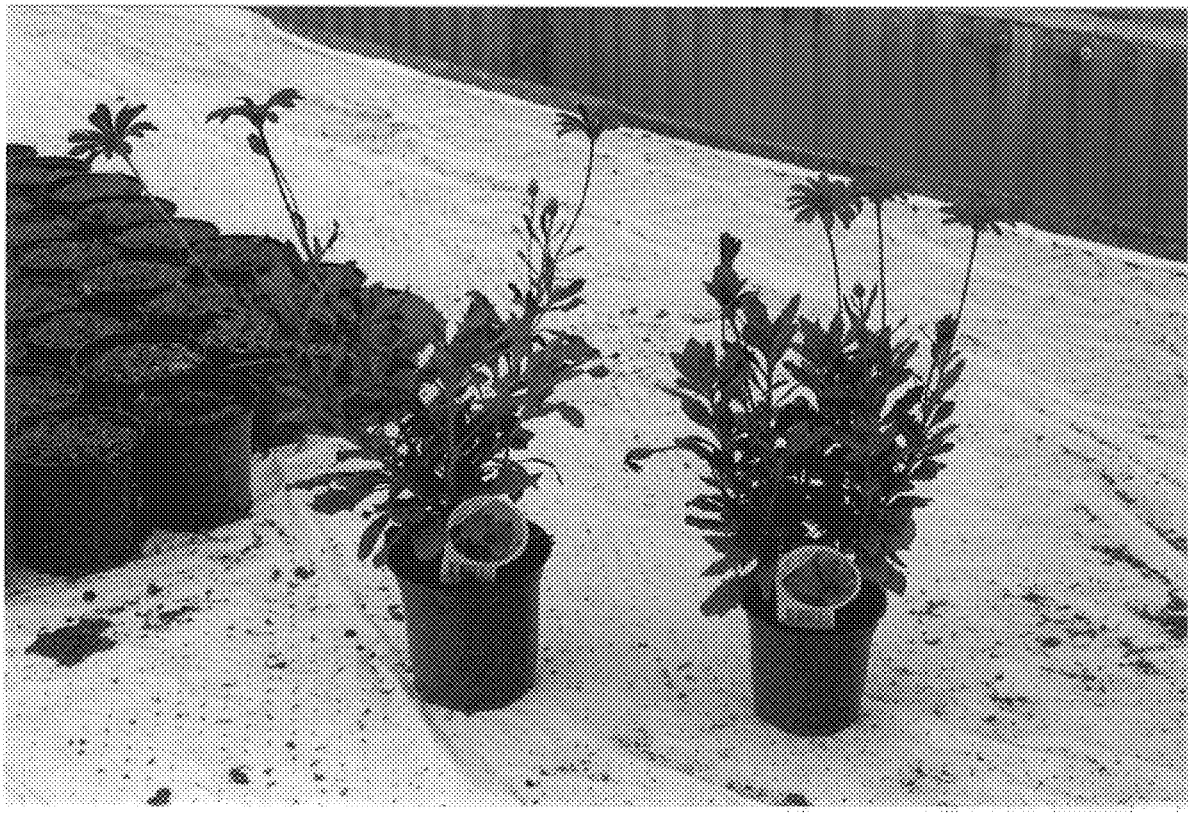

* * * * *